United States Patent [19]

Nakayama et al.

[11] 3,954,880

[45] May 4, 1976

[54] METHOD FOR PRODUCING HIGH-PURITY DICUMYL PEROXIDE

[75] Inventors: Masaharu Nakayama; Isao Hayashi; Makoto Muraguchi, all of Aichi, Japan

[73] Assignee: Nippon Oil and Fats Co., Ltd., Tokyo, Japan

[22] Filed: June 13, 1975

[21] Appl. No.: 586,640

Related U.S. Application Data

[63] Continuation-in-part of Ser. No. 417,051, Nov. 19, 1973, abandoned.

[52] U.S. Cl. .......................... 260/610 A; 260/610 R
[51] Int. Cl.² .......................................... C07C 179/04
[58] Field of Search ....... 417/52; 260/610 A, 610 B, 260/610 R

[56] References Cited

UNITED STATES PATENTS

| | | | |
|---|---|---|---|
| 3,171,860 | 3/1965 | Codignula | 260/610 B |
| 3,367,951 | 2/1968 | Nielsen et al. | 260/610 A |
| 3,639,486 | 2/1972 | Rosenthal et al. | 260/610 R |

*Primary Examiner*—James O. Thomas, Jr.
*Assistant Examiner*—W. B. Lone
*Attorney, Agent, or Firm*—Stevens, Davis, Miller & Mosher

[57] ABSTRACT

High-purity dicumyl peroxide is obtained by mixing a melted crude dicumyl peroxide containing not less than 50% of dicumyl peroxide with an aqueous solution of surfactant, emulsifying the resulting mixture, and cooling the emulsion to a temperature lower than the temperature for solidifying dicumyl peroxide.

6 Claims, No Drawings

METHOD FOR PRODUCING HIGH-PURITY DICUMYL PEROXIDE

This application is a continuation-in-part of our application Ser. No. 417,051, filed Nov. 19, 1973 now abandoned.

The present invention relates to a method for producing dicumyl peroxide (hereinafter abbreviated as DCP) having a high purity of at least 99.0% from crude DCP, and more particularly relates to a method for producing high-purity DCP from crude DCP, which comprises mixing a melted crude DCP containing not less than 50% of DCP with an aqueous solution of surfactant in a concentration and amount sufficient to emulsify the crude DCP, emulsifying the resulting mixture, and cooling the emulsion to a temperature lower than the temperature for solidifying DCP while keeping the emulsified state.

In the present invention, the term "crude DCP" means DCP composition containing not less than 1% (hereinafter "%" means by weight) of an impurity.

Several methods for producing crude DCP have previously been disclosed in patent specifications and other literatures. These methods are, for example, a follows.

1. Self-condensation of cumene hydroperoxide.
2. Condensation of cumene hydroperoxide with α,α-dimethylbenzyl alcohol.
3. Reaction of α,α-dimethylbenzyl alcohol with hydrogen peroxide.
4. Reaction of α-cumyl chloride with hydrogen peroxide.
5. Addition reaction of α-methylstyrene with cumene hydroperoxide.
6. Reaction of cumene with hydroperoxide.
7. Direct oxidation of cumene with oxygen or air.

In any of the above described methods, unreacted raw materials, such as cumene, α-methylstyrene, cumene hydroperoxide, α,α-dimethylbenzyl alcohol, α-cumyl chloride, hydrogen peroxide, etc., by-products, such as acetophenone, α-methylstyrene, phenol, etc., and impurities contained in the raw material, such as n-butylbenzene, t-butylbenzene, etc., are contained in the crude DCP in addition to DCP.

DCP is used in the polymerization reaction of monomers and in the cross-linking reaction of rubber, plastics and the like. However, even when a small amount of impurity is contained in the DCP, the impurity affects adversely on the polymerization reaction and causes the coloration and the deterioration of physical properties in the resulting polymer, and therefore, it is more desirable to use DCP containing smaller amount of impurity. Accordingly, it is necessary to develop a method for purifying DCP from crude DCP in a high purification yield in the commercial production of DCP.

Heretofore, the following methods have been generally used for the purification of DCP.

a. Crude DCP is cooled to crystallize the DCP.
b. Crude DCP is dissolved in solvents, such as methanol, pentane, benzene, a methanol-water system and the like, and the resulting solution is cooled to crystallize the DCP.
c. Impurity is removed from crude DCP by a distillation under a reduced pressure or a steam distillation.

However, these methods have the following drawbacks. In the methods (a) and (b), since the solubility of DCP in the solvent to be used or in the impurity contained in crude DCP is high, the purification yield of DCP decreases. Moreover, in the method (a), impurity adheres to the surface of purified DCP crystal, and in the method (b), the solvent used must be recovered. In the method (c), since crude DCP is heated at the distillation, DCP may be decomposed or colored significantly, and therefore commercial production of high-purity DCP is impossible.

The inventors have made various investigations with respect to the method for producing high-purity DCP from crude DCP, which has not the above described drawbacks of the conventional methods, and surprisingly found out that white fine DCP crystal having a very high purity of at least 99.0% can be obtained by mixing a melted crude DCP with an aqueous solution of surfactant, emulsifying the resulting mixture, cooling the emulsion until the DCP is solidified, while keeping the emulsified state, to crystallize DCP, and subjecting the DCP crystal to washing with water, filtering and drying. However, in this case, when a crude DCP is mixed with an aqueous solution of surfactantt and the resulting mixture is emulsified and the organic layer containing the DCP is merely separated from the water layer at a temperature high than the crystallization temperature of the DCP, the DCP cannot substantially be purified. In the specification and claims, the term "crystallization temperature of DCP" means the temperature, at which DCP contained in a crude DCP is crystallized out from the crude DCP. The inventors have found that only when the above obtained emulsion is cooled to a temperature lower than the crystallization temperature of DCP, the DCP can be purified very effectively, and accomplished the present invention.

As described above, crude DCP contains at least one of benzene derivatives, such as cumene, α-methylstyrene, acetophenone, phenol, α,α-dimethylbenzyl alcohol, cumene hydroperoxide, α-cumyl chloride, n-butylbenzene, t-butylbenzene, etc. as an impurity. Since crude DCP is mainly produced by the above method (2) in industry, crude DCP often contains at least one of cumene, α-methylstyrene, acetophenone, phenol α,α-dimethylbenzyl alcohol and cumene hydroperoxide as an impurity. According to the method of the present invention, high-purity DCP can be obtained by removing all of these impurities from crude DCP.

The crystallization temperature of DCP varies depending upon the composition of crude DCP. For example, the crystallization temperatures of DCP from crude DCPs containing 50, 20, 10 and 1% of impurity are about 0°C, about 23°C, about 29°C and about 37°C, respectively.

Melted DCP is stable without causing serious decomposition and coloration at a temperature of not higher than 80°C, and therefore it is preferable to emulsify crude DCP at a temperature between the crystallization temperature of DCP and 80°C, and it is particularly preferable to emulsify crude DCP at a temperature about 5°C higher than the crystallization temperature of DCP in view of the processability and economy. In the step for crystallizing DCP, it is necessary that the emulsion is cooled to a temperature lower than the crystallization temperature of DCP, and it is preferable to cool the emulsion to a temperature as low as possible in order to crystallize DCP in a high yield. However, in the present invention, it is necessary that the treatment of crude DCP should be effected at a temperature higher than the coagulation temperature of an aqueous solution of surfactant to be used. The coagulation temperature of the aqueous solution of surfactant various depending upon the kind and concentration of the surfactant, but the temperature is usually within the range of $-3°$ to $0°C$.

Accordingly, it is necessary that the concentration of DCP contained in crude DCP should be higher than the concentration (not less than about 50%), at which the DCP is crystallized, at a temperature higher than the coagulation temperature of the aqueous solution of surfactant.

That is, the effect of the present invention appears only when a crude DCP containing 1 to 50% of impurity is mixed with an aqueous solution of surfactant at a temperature between the crystallization temperature of about $0°$ to $37°C$ of DCP and $80°C$, the resulting mixture is emulsified, the emulsion is cooled to a temperature between the coagulation temperature of about $-3°$ to $0°C$ of the aqueous solution of surfactant and the crystallization temperature of about $0°$ to $37°C$ of DCP, while keeping the emulsified state, to crystallize DCP, the resulting DCP crystal is separated, and the separated DCP crystal is washed with water and dried. However, in order to obtain high-purity DCP in a high yield, it is preferable that a crude DCP containing 1 to 20% of impurity is mixed with an aqueous solution of surfactant at a temperature of about $28°$ to $42°C$, which is about $5°C$ higher than the crystallization temperature of DCP, the resulting mixture is emulsified, the emulsion is cooled to a temperature of $0°$ to $5°C$, while keeping the emulsified state, to crystallize DCP, the resulting DCP is separated, and the separated DCP is washed with water and dried. Further, in order to obtain high-purity DCP in a higher yield, it is preferable that a crude DCP containing 1 to 10% of impurity is mixed with an aqueous solution of surfactant at a temperature of about $34°$ to $42°C$, which is about $5°C$ higher than the crystallization temperature of DCP, the resulting mixture is emulsified, the emulsion is cooled to a temperature of $0°$ to $5°C$, while keeping the emulsified state, to crystallize DCP, the resulting DCP crystal is separated, and the separated DCP crystal is washed with water and dried.

The surfactant to be used in the present invention includes any of anionic, cationic, nonionic and ampholytic water-soluble synthetic surfactants having excellent detergency and washing ability, which can be used for both hard water and soft water.

Among them, anionic surfactants of sulfuric acid ester type, sulfonic acid type and phosphoric acid ester type, cationic surfactants of quaternary ammonium salt type and amine derivative type, and nonionic surfactants of polyoxyethylene derivative type, polyhydric alcohol derivative type and alkylol amide derivative type are effective. Particularly, polyoxyethylene nonylphenol ether type nonionic surfactant is effective.

In the present invention, the aqueous solution of surfactant is mixed with crude DCP and the resulting mixture is treated in the form of an emulsion. Accordingly, the aqueous solution of surfactant should have a concentration sufficient to stabilize the emulsion.

The concentration of the aqueous solution of surfactant varies depending upon the kind of surfactant to be used, and therefore it is difficult to define clearly the ranges of the concentration and amount of the aqueous solution of surfactant suitable for the purification of crude DCP, but the concentration and amount, by which crude DCP is wholly emulsified, are required.

The most suitable kind, concentration and amount of the aqueous solution of surfactant to be used in the purification of crude DCP can be easily determined by a simple preliminary test.

In the present invention, aqueous solution containing a surfactant in a concentration of 0.005 to 2% is generally used. When the concentration of surfactant is less than 0.005%, s the effect of the present invention does not appear, and when the concentration is more than 2%, the purification system is excessively emulsified, and the separation of DCP crystal becomes difficult. The optimum concentration of a surfactant in aqueous solution is generally 0.05 to 0.5%.

In general, the aqueous solution of surfactant is used effectively in an amount of 1 to 100 parts by weight, and most effectively in an amount of 2 to 20 parts by weight, based on 1 part by weight of crude DCP.

When the method of the present invention is applied to a crude DCP containing not less than 50% of DCP by using the most suitable kind of aqueous solution of surfactant in the most suitable amount and concentration, the crude DCP can be purified and white fine DCP crystal having a high purity can be obtained. However, when a large amount of impurity is contained in a crude DCP, even if the crude DCP is cooled to a temperature lower than the crystallization temperature of DCP, a large amount of DCP is dissolved in the emulsion of the impurity due to the high solubility of DCP in the impurity, and the development of solid DCP colloid is poor, and as the result the yield of DCP crystal decreases. Accordingly, the DCP concentration in a crude DCP is preferred to be higher to order to purify DCP contained in the crude DCP in a high yield by the method of the present invention. In the commercial production of DCP, it is often difficult to obtain crude DCP having a high DCP concentration depending upon the purity of raw materials and the formation of by-products. In this case, it is desirable that crude DCP is concentrated to increase the DCP concentration in order to increase the yield of DCP crystal.

The following examples are given for the purpose of illustration of this invention and are not intended as limitations thereof.

EXAMPLE 1

50 g of a melted DCP containing 97.4% of DCP and further 0.1% of cumene, 0.1% of $\alpha$-methylstyrene, 0.3% of acetophenone, 1.7% of $\alpha,\alpha$-dimethylbenzyl alcohol and 0.4% of cumene hydroperoxide as an impurity was added to an aqueous solution of NISSAN NONION NS-210 (Trademark of a polyoxyethylene nonylphenol ether type nonionic surfactant made by Nippon Oils and Fats Co.), the concentration and addition amount of which were shown in the following Table 1, and the resulting mixture was emulsified and then cooled from $40°C$ to $5°C$ while keeping the emulsified state. The resulting white fine DCP crystal was filtered and dried to obtain results as shown in Table 1.

Table 1 shows the concentration and amount of NISSAN NONION NS-210 used, the purity and melting point of the purified DCP crystal, and the purification yield of the DCP.

Table 2 shows the kind of surfactants used, the purity and melting point of the purified DCP crystal, and the purification yield of the DCP.

Table 2

| Surfactant | | | Purity of DCP crystal (%) | Melting point of DCP crystal (°C) | Purification yield of DCP (%) |
|---|---|---|---|---|---|
| Trademark | Type | Structure or composition | | | |
| NISSAN NONION NS-210 | nonionic | polyoxyethylene nonylphenol ether | 99.8 | 38.5–39.5 | 98.2 |
| NISSAN NONION O-6 | nonionic | polyoxyethylene monooleate | 99.7 | 38.3–39.2 | 95.4 |
| NISSAN PLONON No. 201 | nonionic | HO(CH$_2$CH$_2$O)$_m$(CHCH$_3$CH$_2$—O)$_n$(CH$_2$CH$_2$O)$_n$H | 99.5 | 38.2–39.2 | 94.2 |
| NISSAN TRAX K-40 | anionic | polyether sulfate | 99.7 | 38.6–39.4 | 96.3 |
| NISSAN DIAPON S | anionic | oleic amide sulfonate | 99.7 | 38.5–39.4 | 95.7 |
| NISSAN SINTREX | anionic | sodium salt of sulfuric acid ester of higher alcohol | 99.6 | 38.4–39.4 | 93.8 |
| NISSAN CATION BB | cationic | dodecyltrimethylammonium chloride | 99.7 | 38.4–39.3 | 96.0 |
| NISSAN NYMEEN T2-206 | cationic | polyoxyethylene-tallow-alkylamine | 99.7 | 38.3–39.3 | 92.0 |
| NISSAN ANON BF | ampholytic | dimethyl-coco-alkylbetaine | 99.6 | 38.3–39.4 | 94.3 |

Table 1

| Aqueous solution of NISSAN NONION NS-210 | | Purity of DCP crystal (%) | Melting point of DCP crystal (°C) | Purification yield of DCP (%) |
|---|---|---|---|---|
| Concentration (%) | Amount (g) | | | |
| 0.05 | 500 | 99.7 | 38.7–39.5 | 95.0 |
| 0.1 | 500 | 99.7 | 38.5–39.5 | 95.0 |
| 0.2 | 100 | 99.6 | 38.4–39.4 | 96.9 |
| 0.2 | 250 | 99.7 | 38.3–39.4 | 91.9 |
| 0.2 | 500 | 99.9 | 38.8–39.7 | 92.1 |
| 0.2 | 1,000 | 99.9 | 39.5–40.0 | 93.2 |
| 0.3 | 500 | 99.8 | 39.4–4.0 | 94.1 |
| 0.4 | 500 | 99.9 | 39.2–39.8 | 94.2 |

EXAMPLE 2

100 g of a melted crude DCP containing 71.4% of DCP and further 8.3% of cumene, 1.9% of α-methylstyrene, 1.9% of phenol, 1.1% of acetophenone, 11.4% of α,α-dimethylbenzyl alcohol and 4.0% of cumene hydroperoxide as an impurity was mixed with 4,000 g of a 0.2% aqueous solution of NISSAN NONION NS-210, and the resulting mixture was cooled from 25°C to 0°C while emulsifying the mixture. The resulting white fine DCP crystal was filtered and dried to obtain 36 g of DCP having a purity of 99.7%.

The purification yield of the DCP was 50.4% and the melting point of the purified DCP crystal was 38.4° to 39.4°C.

EXAMPLE 3

50 g of a melted crude DCP containing 95.7% of DCP and further 0.1% of cumene, 0.5% of acetophenone, 2.9% of α,α-dimethylbenzyl alcohol and 0.8% of cumene hydroperoxide as an impurity was mixed with 500 g of a 0.2% aqueous solution of a surfactant as shown in the following Table 2 at 40°C, and the resulting mixture was cooled to 5°C while emulsifying the mixture. The resulting white fine DCP crystal was washed with water, filtered and dried to obtain results as shown in Table 2.

All the surfactants shown in the above Table 2 are made by Nippon Oils and Fats Co.

The following comparative examples are given in order to show the merit of the present invention.

COMPARATIVE EXAMPLE 1

100 g of a melted crude DCP containing 90.7% of DCP and further 0.3% of cumene, 0.9% of α-methylstyrene, 1.3% of acetophenone, 6.2% of α,α-dimethylbenzyl alcohol and 0.6% of cumene hydroperoxide as an impurity was emulsified in 1,000 g of water at 40°C and the resulting emulsion was cooled to 5°C while keeping the emulsified state.

The resulting DCP crystal was filtered and dried to obtain 84.2 g of yellow DCP crystal having a purity of 97.2%, which contained 0.1% of cumene, 0.1% of α-methylstyrene, 0.4% of acetophenone, 2.0% of α,α-dimethylbenzyl alcohol and 0.2% of cumene hydroperoxide as an impurity.

The purification yield of the DCP was 90.2% and the melting point of the purified DCP was 36.4° to 38.8°C.

Even when the crystallization process of DCP, wherein the above obtained yellow DCP crystal was melted and emulsified in water at 40°C and the resulting emulsion was cooled while keeping the emulsified state, was repeated, the color and the impurity of the DCP were not able to be removed.

COMPARATIVE EXAMPLE 2

100 g of a melted crude DCP containing 90.7% of DCP and further 0.3% of cumene, 0.9% of α-methylstyrene, 1.3% of acetophenone, 6.2% of α,α-dimethylbenzyl alcohol and 0.6% of cumene hydroperoxide as an impurity was mixed with 1,000 g of a 0.2% aqueous solution of NISSAN NONION NS-210 at 40°C, and the resulting mixture was emulsified and subjected to a centrifugation without cooling. The separated organic layer was composed of DCP having a purity of only 91.3%, which contained 0.3% of cumene, 0.9% of α-methylstyrene, 1.2% of acetophenone, 5.6% of α,α-dimethylbenzyl alcohol and 0.7% of cumene hydroperoxide as an impurity.

The purification yield of the DCP was 94.6%.

What is claimed is:

1. A method for producing dicumyl peroxide having a high purity of at least 99.0% from crude dicumyl peroxide, which comprises mixing 1 part by weight of a crude dicumyl peroxide containing 1 to 50% by weight of at least one of benzene derivatives, such as cumene, α-methylstyrene, acetophenone, phenol, α,α-dimethylbenzyl alcohol, cumene hydroperoxide, α-cumyl chloride, n-butylbenzene and t-butylbenzene, as an impurity with 1 to 100 parts by weight of a 0.005 to 2% by weight solution of a water-soluble synthetic surfactant in water at a temperature between the crystallization temperature of about 0° to 37°C of dicumyl peroxide and 80°C, emulsifying the resulting mixture, cooling the emulsion to a temperature between the coagulation temperature of about −3° to 0°C of the above described aqueous solution of surfactant and the above described crystallization temperature of dicumyl peroxide, while keeping the emulsified state, to crystallize dicumyl peroxide, separating the dicumyl peroxide crystal, and subjecting the separated dicumyl peroxide crystal to washing with water and drying.

2. The method according to claim 1, wherein said water-soluble synthetic surfactant is a member selected from the group consisting of anionic surfactants of sulfuric acid ester type, sulfonic acid type and phosphoric acid ester type, cationic surfactants of quaternary ammonium salt type and amine derivative type, and nonionic surfactants of polyoxyethylene derivative type, polyhydric alcohol derivative type and alkylolamide derivative type.

3. The method according to claim 1, wherein said crude dicumyl peroxide contains at least one of cumene, α-methylstyrene, acetophenone, phenol, α,α-dimethylbenzyl alcohol and cumene hydroperoxide as an impurity.

4. The method according to claim 3, wherein 1 part by weight of crude dicumyl peroxide containing 1 to 20% by weight of impurity is mixed with 2 to 20 parts by weight of a 0.05 to 0.5% by weight solution of a water-soluble synthetic surfactant in water at a temperature of about 28° to 42°C, which is about 5°C higher than the crystallization temperature of dicumyl peroxide, the resulting mixture is emulsified, the emulsion is cooled to a temperature of 0° to 5°C while keeping the emulsified state.

5. The method according to claim 4, wherein 1 part by weight of a crude dicumyl peroxide containing 1 to 10% by weight of impurity is mixed with 2 to 20 parts by weight of the aqueous solution of surfactant at a temperature of about 34° to 42°C, which is about 5°C higher than the crystallization temperature of dicumyl peroxide.

6. The method according to claim 5, wherein said surfactant is polyoxyethylene nonylphenol ether type nonionic surfactant.

* * * * *